(12) United States Patent
Fassa

(10) Patent No.: US 11,844,871 B2
(45) Date of Patent: Dec. 19, 2023

(54) METHOD FOR SANITIZING THE SAND OF A BEACH OR OF A STRAND

(71) Applicant: FASSA S.R.L., Spresiano (IT)

(72) Inventor: Paolo Fassa, Spresiano (IT)

(73) Assignee: FASSA S.R.L., Spresiano (IT)

(*) Notice: Subject to any disclaimer, the term of this patent is extended or adjusted under 35 U.S.C. 154(b) by 461 days.

(21) Appl. No.: 15/733,951

(22) PCT Filed: Mar. 1, 2019

(86) PCT No.: PCT/EP2019/055175
§ 371 (c)(1),
(2) Date: Dec. 1, 2020

(87) PCT Pub. No.: WO2019/228685
PCT Pub. Date: Dec. 5, 2019

(65) Prior Publication Data
US 2021/0228755 A1    Jul. 29, 2021

(30) Foreign Application Priority Data

Jun. 1, 2018 (IT) .................... 102018000005928

(51) Int. Cl.
*A61L 2/23* (2006.01)
*E01H 12/00* (2006.01)

(52) U.S. Cl.
CPC .............. *A61L 2/23* (2013.01); *E01H 12/002* (2013.01); *A61L 2202/16* (2013.01)

(58) Field of Classification Search
CPC ....................................................... A61L 2/23
See application file for complete search history.

(56) References Cited

FOREIGN PATENT DOCUMENTS

| JP | H10-179698 A | 7/1998 |
|---|---|---|
| KR | 20120003675 U | 5/2012 |
| WO | WO 91/17318 A1 | 11/1991 |

OTHER PUBLICATIONS

Hashemi et al. Lime-treatment of sand improved by bentonite addition .Conference: European Young Technical Engineers Conference (EYGEC) Jan. 2012. (Year: 2012).*
English Machine Translation of Yamaoka et al. JPH10179698.Jul. 7, 1998 (Year: 1998).*
International Search Report and Written Opinion dated Apr. 12, 2019 issued in PCT/EP2019/055175.
Italian Search Report dated Mar. 21, 2019 issued in IT 201800005928, with partial translation.

* cited by examiner

*Primary Examiner* — Donald R Spamer
(74) *Attorney, Agent, or Firm* — Scully, Scott, Murphy & Presser, P.C.

(57) ABSTRACT

A method for sanitizing the sand of a beach or strand, comprising a step of scattering on the sand to be treated at least one first layer of lime, followed by a step of mechanical mixing of the sand treated with the lime. It is then optionally possible to repeat the two preceding steps to then move on to a step of mechanical ventilation of the sand treated with the lime.

7 Claims, 4 Drawing Sheets

METHOD FOR SANITIZING THE SAND OF A BEACH OR OF A STRAND

The present invention relates to a method for sanitizing the sand of a beach or of a strand.

Currently the fact is known that on beaches there is a problem from the hygienic and sanitary standpoint which is due to the presence, on or in the sand, of pollution which renders beaches unfit for bathing and therefore not usable; there is also a further problem if the presence of algae is detected on beaches, since they tend to rot, generating bad odors, in a short time. The optional use of labor to clean the beaches is uneconomical, since it would require a very long time.

As a partial solution to these drawbacks it is known to partially clean beaches by passing a harrow on the sand: however, this allows to remove bulky waste, at the same time ventilating the sand, which as is known has a particle size comprised between 2 and 0.063 mm.

However, this solution does not solve the problem, since only the bulkiest foreign objects are removed, such as for example branches, bottles, large plastic parts, algae, while the smaller components are not removed and in addition they are mixed in with the sand, making it even more difficult, if not impossible, to optionally subsequently remove them.

As a partial solution to these problems it is known to use earth-moving machines provided with a front bucket with which removal of the elements that arise from the sand is attempted; this solution, used particularly to remove for example algae which clump together forming small piles, still has drawbacks, since it is inevitable to remove sand as well, thus depleting the strand and accordingly creating a further drawback owing to the known problem of the constant erosion of beaches.

The aim of the present invention is therefore to solve the described technical problems, eliminating the drawbacks of the cited background art and thus providing a method that allows to sanitize the sand of a beach or of a strand rapidly and easily.

Within this aim, an object of the invention is to provide a method that allows in particular to treat the sand by sanitizing polluting or biodegradable products, such as for example algae.

Another object of the invention is to define a method that allows in particular to treat the sand by sanitizing even very small products, which cannot be removed mechanically according to the described background art.

Another object of the invention is to obtain a method that can be used rapidly on strands, allowing to sanitize large areas thereof, and at low sanitizing costs.

This aim and these and other objects which will become better apparent hereinafter are achieved by a method for sanitizing the sand of a beach or of a strand, characterized in that it comprises the steps of:
- scattering on the sand to be treated at least one first layer of lime
- mechanically mixing said sand treated with said lime
- optionally repeating the two preceding steps
- mechanically ventilating said sand treated with said lime.

Further characteristics and advantages of the invention will become better apparent from the detailed description of a particular but not exclusive embodiment, illustrated by way of nonlimiting example in the accompanying drawing, wherein.

Figure 1:
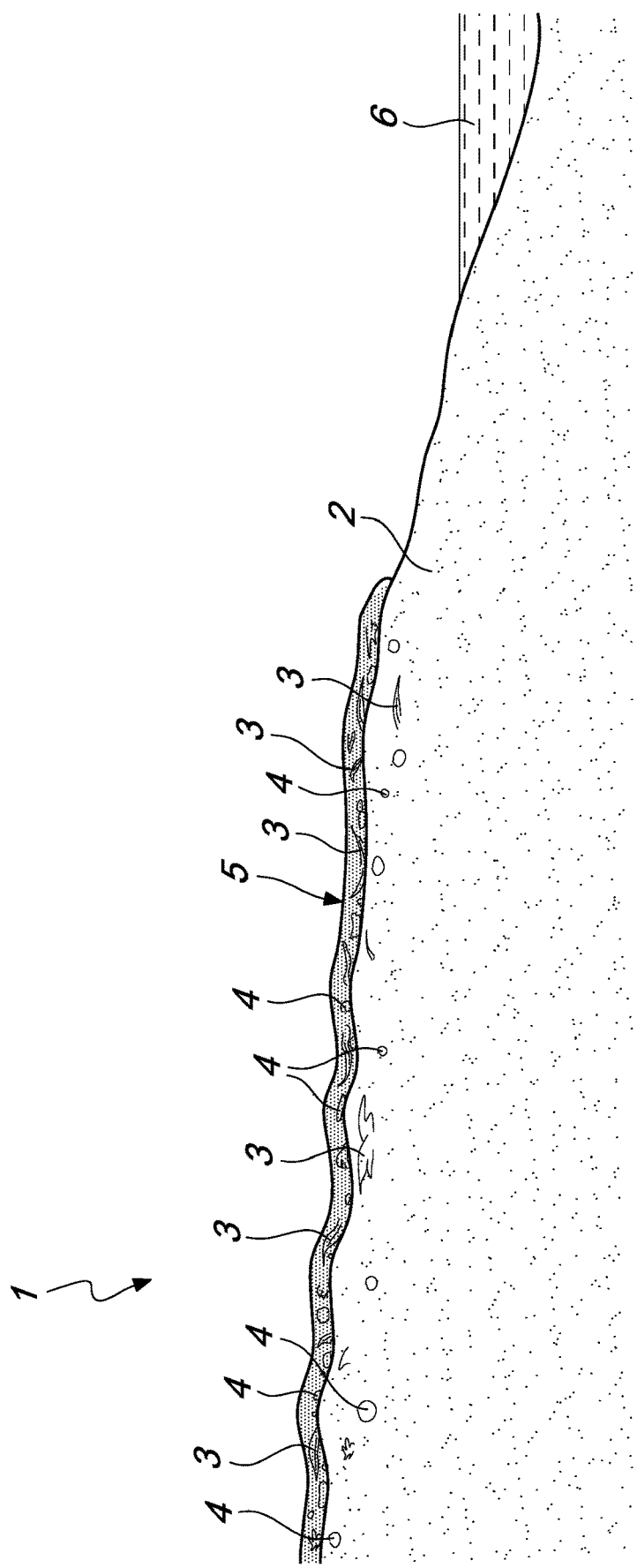
FIG. 1 is a schematic view of the step of the scattering of a layer of lime on the sand to be treated.
Figure 2:
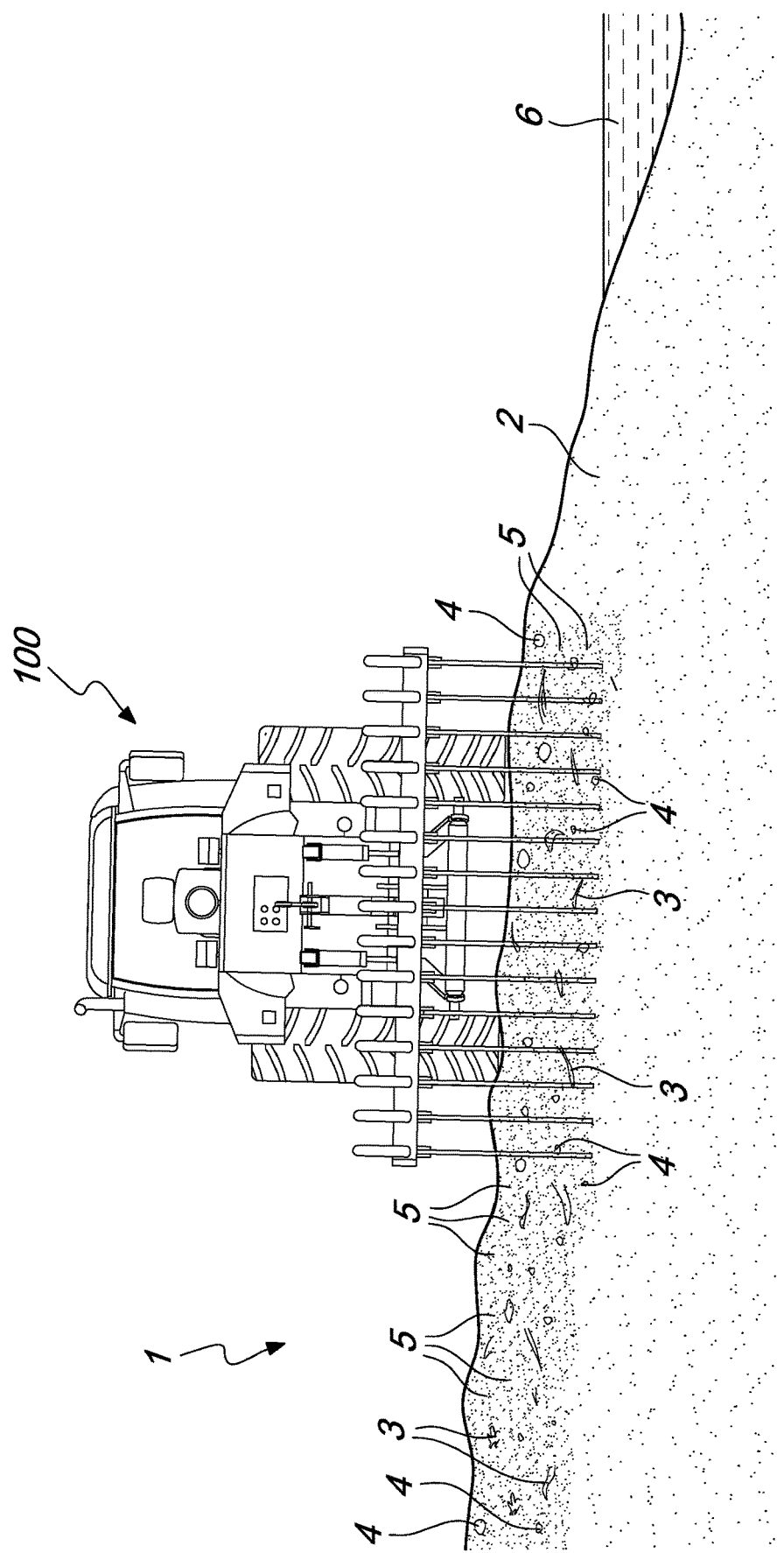
FIG. 2 is a schematic view of the subsequent step of mechanical mixing of the previously treated sand.
Figure 3:
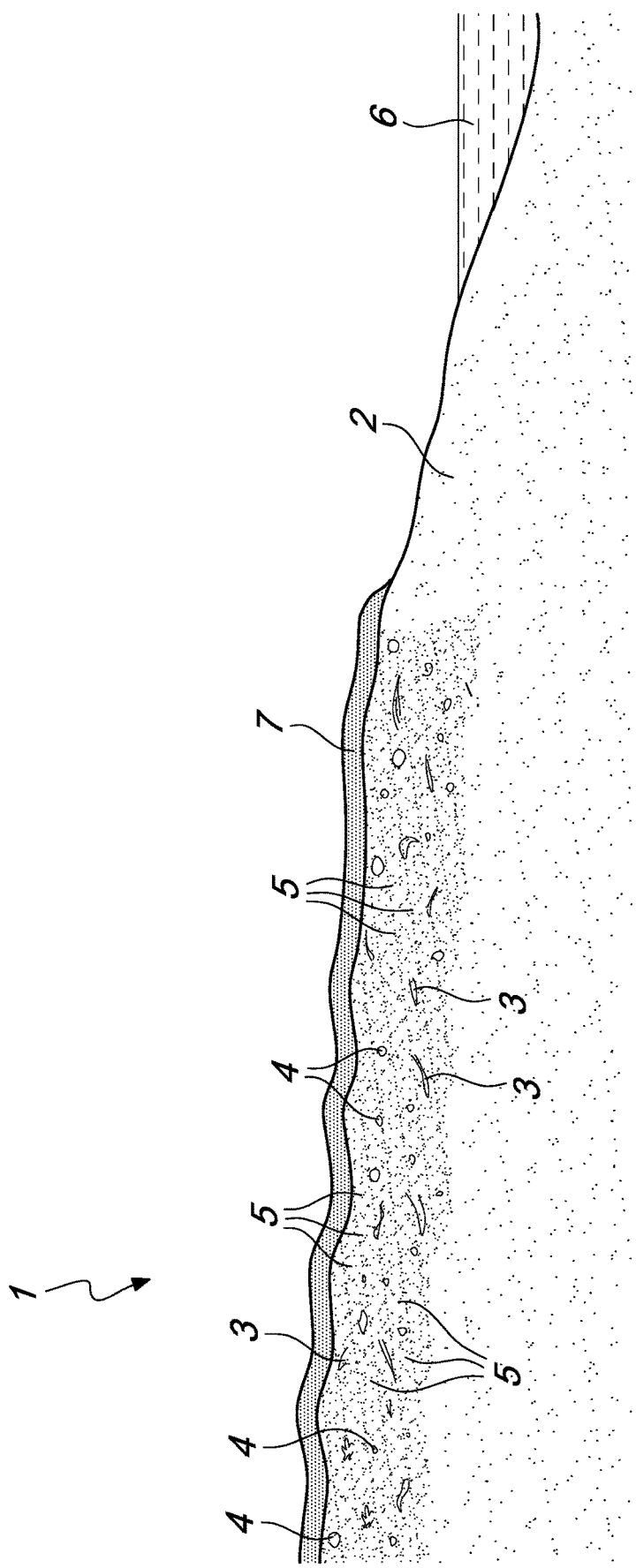
FIG. 3 is a schematic view of an optional subsequent step of further scattering of another layer of lime on the previously treated sand.
Figure 4:
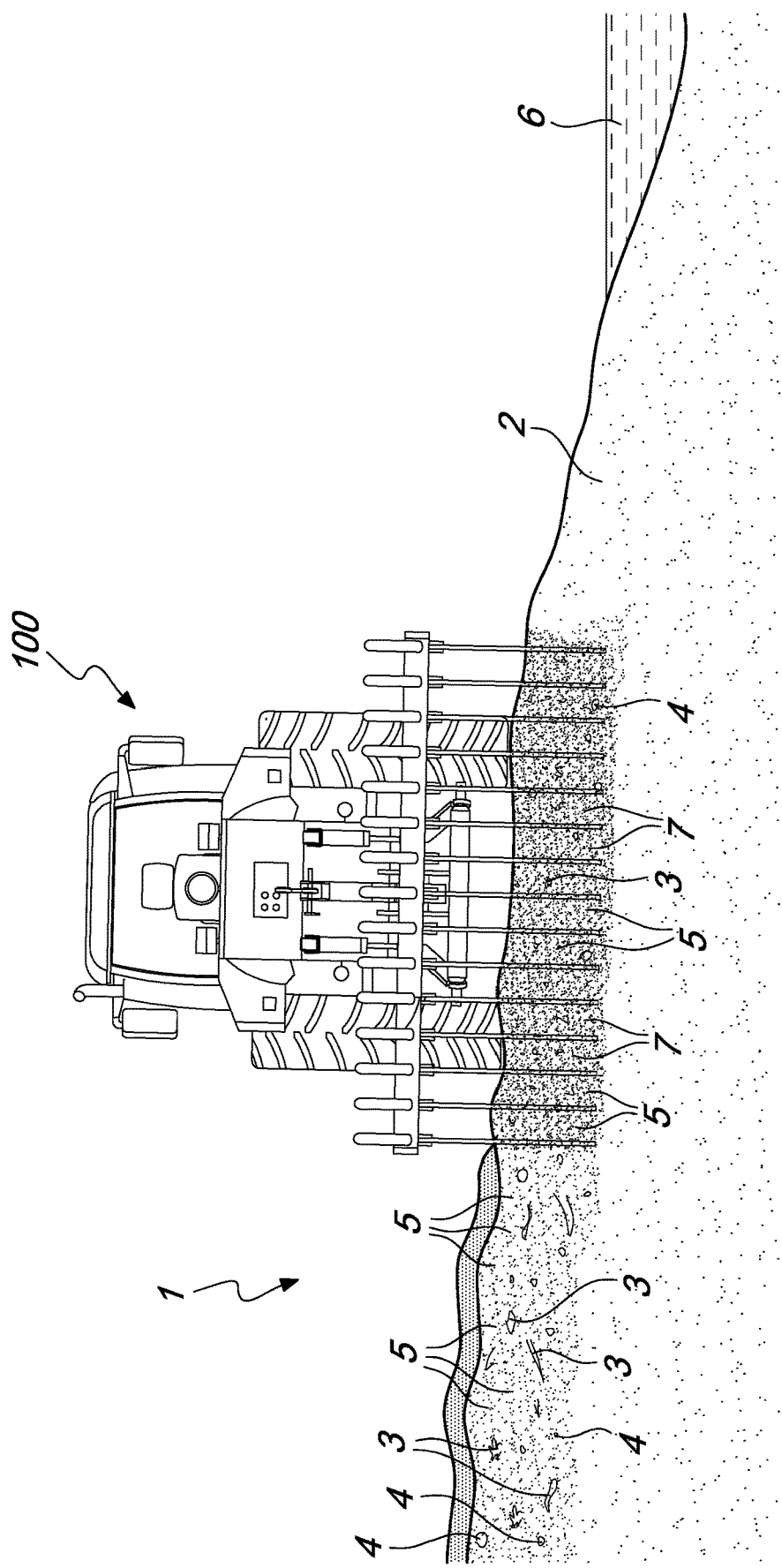
FIG. 4 is a view of the step of mechanical ventilation of the sand treated with the lime.

In the following exemplary embodiments, individual characteristics, given in relation to specific examples, may actually be interchanged with other different characteristics that exist in other exemplary embodiments.

With reference to the figures, the reference numeral 1 designates a beach or strand, the sand 2 of which is contaminated, for example by algae 3 and/or microorganisms and/or biodegradable products and/or even very small products, all designated by the reference numeral 4.

The method for sanitizing the sand 2 of the beach or strand 1 comprises a first step, in which at least one first layer 5 of lime is scattered on the sand 2 to be treated, with a quantity preferably comprised between 20 and 30 kg/m$^3$ of sand 2 to be treated.

The doses of lime will of course vary as a function of the type of bacterial load and/or of any pollutants (heavy metals or others) that are present in the sand.

The lime is thus deposited on the elements 3, 4 that have contaminated the sand.

The scattering of the lime can occur for example by means of a lime spreading device of a known type.

It is possible, for example, to use dolomitic lime (which is essentially a dry white powder, obtained by treating dolomitic quicklime with water in a quantity that is sufficient to satisfy its chemical affinity to hydrate and is constituted for example by calcium hydroxide, magnesium hydroxide and magnesium oxide) or calcitic lime; the former is more bland, while the latter can be used for example for strands that require more intense sanitizing.

The scattering of the lime by using machines of a known type, which are not shown, may thus affect portions at least two meters wide, with the refinement of performing the treatments at an appropriate distance from the water 6, preferably two meters away from it.

The lime doses will vary as a function of the type of bacterial load and/or of any pollutants (heavy metals or others).

The method furthermore provides for a second step, in which the previously treated sand is mixed mechanically with said lime for example by means of a harrow with blades 100, which is towed or self-propelled, of a known type.

The mechanical mixing of the sand occurs for a variable depth, preferably of at least thirty centimeters.

The method then provides for the possibility to repeat the preceding steps, for example the scattering of a second layer 7 of lime on the sand 2 to be treated.

Finally, the method provides for performing mechanical ventilation of said sand 2 treated with said lime so as to ventilate the treated region.

Ventilation can occur for example by means of the same harrow with blades 100.

Since the use of lime entails controlling the treated area, it is preferable to forbid bathing at the beach being treated for a period comprised for example between thirty and sixty days, and therefore the treatment of the sand is performed preferably in the winter period.

The lime, thus mixed with the various pollutants and with the sand, over time will sanitize the sand itself, thus making the beach fit for bathing.

It has thus been found that the invention has achieved the intended aim and objects, a method having been obtained which allows to sanitize the sand of a beach or of a strand rapidly and easily, eliminating pollutant or biodegradable products, such as for example algae and polluting products of even very small size, which cannot be removed mechanically according to the described background art.

Furthermore, the method can be used rapidly for large portions of beach, allowing to sanitize large areas thereof with low sanitizing costs.

The materials used, as well as the dimensions that constitute the individual components of the invention, may of course be more pertinent according to the specific requirements.

The characteristics indicated as advantageous, convenient or the like may also be omitted or be replaced with equivalents.

The disclosures in Italian Patent Application No. 102018000005928 from which this application claims priority are incorporated herein by reference.

The invention claimed is:

1. A method for sanitizing sand of a beach or strand, comprising the steps of:
   scattering on the sand to be treated at least one first layer of lime;
   mechanically mixing said sand treated with said lime;
   optionally repeating the two preceding steps;
   mechanically ventilating said sand treated with said lime;
   wherein said step of mechanical mixing of said sand treated previously with said lime occurs for a variable depth.

2. The method according to claim 1, wherein said first step of scattering said at least one first layer of lime on said sand to be treated occurs by using a quantity of lime that is comprised between 20-30 kg per cubic meter of sand to be processed.

3. The method according to claim 1, wherein said scattering of said lime occurs by means of a lime spreading device.

4. The method according to claim 1, wherein said lime is of dolomitic and/or calcitic type.

5. The method according to claim 1, wherein said step of mechanical mixing of said sand previously treated with said lime occurs for a depth of at least thirty centimeters.

6. The method according to claim 1, wherein said method comprises scattering a second layer of lime and repeating said mechanical mixing step.

7. The method according to claim 1, wherein said mechanical ventilation of said sand treated with said lime occurs by milling with a harrow with multiple plows which is towed or self-propelled.

* * * * *